United States Patent
Augustijn et al.

(10) Patent No.: US 6,910,084 B2
(45) Date of Patent: Jun. 21, 2005

(54) METHOD AND SYSTEM FOR TRANSFERRING AND STORING DATA IN A MEDICAL DEVICE WITH LIMITED STORAGE AND MEMORY

(75) Inventors: Frederik Augustijn, AK Arnhem (NL); Lucas J. J. M. Meekes, CN Spankeren (NL); Harry B. A. Kerver, NZ Duiven (NL)

(73) Assignee: Medtronic, Inc, Minneapolis, MN (US)

( * ) Notice: Subject to any disclaimer, the term of this patent is extended or adjusted under 35 U.S.C. 154(b) by 432 days.

(21) Appl. No.: 09/843,915

(22) Filed: Apr. 30, 2001

(65) Prior Publication Data

US 2002/0188773 A1 Dec. 12, 2002

(51) Int. Cl.[7] .............................................. G06F 13/00
(52) U.S. Cl. ............................. 710/52; 710/4; 710/20; 710/33; 710/53
(58) Field of Search ............................... 710/4, 20, 33, 710/52, 53

(56) References Cited

U.S. PATENT DOCUMENTS

| | | |
|---|---|---|
| 4,375,817 A | 3/1983 | Engle et al. |
| 4,379,459 A | 4/1983 | Stein |
| 4,384,585 A | 5/1983 | Zipes |
| 4,476,868 A | 10/1984 | Thompson et al. |
| 4,556,063 A | 12/1985 | Thompson et al. |
| 4,577,633 A | 3/1986 | Berkovits et al. |
| 4,587,970 A | 5/1986 | Holley |

(Continued)

OTHER PUBLICATIONS

"Onset and Stability for Ventricular Tachyarrhythmia Detection in an Implantable Pacer–Cardioverter–Defibrillator" Olson et al., Computers in Cardiology, Oct. 7–10, 1986, IEEE Computer Society Press, pp 167–170.

*Primary Examiner*—Jeffrey Gaffin
*Assistant Examiner*—Mohammad O. Farooq
(74) *Attorney, Agent, or Firm*—Girma Wolde-Michael; Daniel G. Chapik

(57) ABSTRACT

A method of transferring at least two data streams in a medical device is provided. First data stream data is collected into a first intermediate register. Additional data stream data is collected into an additional intermediate register. First intermediate register contents are stored in at least one first output register. Systems and devices for using the method are also provided.

49 Claims, 8 Drawing Sheets

U.S. PATENT DOCUMENTS

| | | | |
|---|---|---|---|
| 4,716,903 A | | 1/1988 | Hansen et al. |
| 4,726,380 A | | 2/1988 | Vollmann |
| 4,727,877 A | | 3/1988 | Kallok |
| 4,800,005 A | | 1/1989 | Rosenfield et al. |
| 4,800,883 A | | 1/1989 | Winstrom |
| 4,843,544 A | * | 6/1989 | DuLac et al. ................. 710/53 |
| 4,920,489 A | | 4/1990 | Hubelbank et al. |
| 4,949,719 A | | 8/1990 | Pless |
| 4,953,551 A | | 9/1990 | Mehra |
| 5,088,025 A | * | 2/1992 | Fujimoto .................... 710/52 |
| 5,117,824 A | | 6/1992 | Keimel et al. |
| 5,144,949 A | | 9/1992 | Olson |
| 5,158,078 A | | 10/1992 | Bennett et al. |
| 5,163,424 A | | 11/1992 | Kohnke |
| 5,197,145 A | * | 3/1993 | Kitamura et al. ........... 711/143 |
| 5,199,428 A | | 4/1993 | Obel et al. |
| 5,207,218 A | | 5/1993 | Carpentier et al. |
| 5,215,098 A | | 6/1993 | Steinhaus et al. |
| 5,217,021 A | | 6/1993 | Steinhaus et al. |
| 5,263,486 A | | 11/1993 | Jeffreys |
| 5,312,446 A | | 5/1994 | Holschbach et al. |
| 5,312,453 A | | 5/1994 | Shelton et al. |
| 5,330,507 A | | 7/1994 | Schowartz |
| 5,331,966 A | | 7/1994 | Bennett et al. |
| 5,354,316 A | | 10/1994 | Keimel et al. |
| 5,410,727 A | * | 4/1995 | Jaffe et al. ................... 709/234 |
| 5,455,820 A | * | 10/1995 | Yamada ................. 370/395.71 |
| 5,545,186 A | | 8/1996 | Olson |
| 5,603,331 A | | 2/1997 | Heemels et al. |
| 5,623,935 A | | 4/1997 | Faisandier |
| 5,694,356 A | | 12/1997 | Wong et al. |
| 5,709,216 A | | 1/1998 | Woodson et al. |
| 5,735,285 A | | 4/1998 | Albert et al. |
| 5,779,634 A | * | 7/1998 | Ema et al. ................. 600/407 |
| 5,800,456 A | | 9/1998 | Maeda et al. |
| 5,819,740 A | | 10/1998 | Muhlenberge et al. |
| 5,836,889 A | | 11/1998 | Wyborny et al. |
| 5,836,982 A | | 11/1998 | Muhlenberge et al. |
| 6,147,628 A | * | 11/2000 | Dyche et al. ................. 341/60 |
| 6,306,088 B1 | * | 10/2001 | Krausman et al. .......... 600/301 |

* cited by examiner

METHOD AND SYSTEM FOR TRANSFERRING AND STORING DATA IN A MEDICAL DEVICE WITH LIMITED STORAGE AND MEMORY

FIELD OF THE INVENTION

The present invention relates to the field of medical devices with limited data storage and memory capacity. More particularly, the present invention relates to implantable medical devices, such as cardiac pacing devices, that are capable of transferring and storing data, such as heart signal data, in the form of two or more streams of data with variable sample size and/or variable rate.

BACKGROUND OF THE INVENTION

Medical devices with limited data storage and memory capacity are well known in the art. Two common examples of such devices are hearing aids and pacemakers. Pacemakers or other such implantable pulse generators (IPGs) in particular have requirements for storage and transfer of data that sometimes exceeds the storage and memory capacity available. Some IPGs include means for storing data related to cardiac events such as episodes of spontaneous heart rate that are higher or lower than an acceptable or previously established rate. Stored data related to one or more cardiac events are useful in assessing the functioning of the IPG and in monitoring the progress of the patient.

Digital signal processing (DSP) has proved to be a useful tool in the environment of implantable medical devices such as implantable pulse generators. Using DSP technology, an incoming sensed heart signal may be converted to a digital signal, e.g., an 8-bit signal. This conversion may occur at a predetermined sample rate. For example, episodes of Intracardiac Electro Cardiogram (IEGM) may be processed using DSP. The IEGM is one type of signal in which heart contractions may be identified.

Typically an input signal from an IPG is amplified. The signal may then be converted to a digital signal (using, for example, A/D, or analog to digital converters). Then the signal may be digitally processed, generally by filtering the resulting digital data streams. The result from this process is generally a number of digital data streams. Each data stream is more or less a digitally processed representation of an IPG input signal. Based upon the information in these streams, DSP technology may be used to determine heart contractions. As stated above, a physician may use information about these contractions to assess and monitor the efficacy of IPG therapy.

Typically, data is collected continuously while the patient is using the IPG. A physician is only able to view the data when the patient and the IPG are available for evaluation, e.g. when the patient is in the physician's office. At that time, the IPG may be linked to an interrogation device with a display, which shows the data being collected at the time the patient is being examined.

However, the most interesting episodes of IEGM generally occur when the patient is proceeding about his normal business away from the physician's office. Thus, some IPGs (and other implantable therapeutic devices) have the capability to store data, such as an IEGM, for later viewing by the physician. At the time of viewing, the IPG may be linked to an interrogation device with a display that communicates the stored data. Because implantable devices are, of necessity, small enough for implantation in a human body, their available storage space is limited. Thus, the data, such as a digital IEGM, needs to be compressed as much as possible without losing the sense of the original signal.

In a typical compression method, more than one data stream may be received and/or processed (e.g. transferred, transmitted, compressed or stored, etc.) at a given time. Sometimes, the data streams may arrive at different rates. Storage of more than one data stream, particularly if the streams arrive at different rates may require significant amounts of memory. For example, two data streams may start out with the same fixed width (e.g. each sample may be 8 bits wide) and a fixed sample rate, which is the number of signal (sample) values being received or processed per unit of time, (e.g. each sample may be transmitted at a sample rate of 200 transmit units per second). However, after the data streams are compressed, the width and sample rate of the two streams may differ.

For example, data stream 1 and data stream 2 may both be 8 bits wide prior to compression. However, after compression, one data value of data stream 1 may be reduced to a single bit whereas one data value of data stream 2 has been reduced to 5 bits.

After compression, the streams may be combined into one 16-bit word, and transferred to Random Access Memory (RAM). This may be accomplished using Direct Memory Access (DMA) which transfers the data to RAM without using a microprocessor or Central Processing Unit (CPU). A DMA unit may be programmed to transfer a fixed amount of data (for example, the 16-bit word described above) from a data source to a destination, such as RAM. Thus, DMA transfer occurs at a fixed rate (in the above case, 16 bits per unit of time.) However, the data arriving to be transferred via DMA from data stream 1 and data stream 2 continues to arrive at variable rates after compression, depending on the content of the signal. Moreover, it is necessary to track the components of each word that originally belonged to each respective signal.

Several methods may be used to overcome this difference in rates at which the data streams arrive. A first-in, first-out buffer could be used, for example, on the chip used to conduct the DMA transfer. In this case, data stream 1 is transferred until the buffer is full or until all data has been transferred to the buffer from stream 1. If any space is left in the buffer, data stream 2 is then transferred until the buffer is full. Otherwise, the buffer is emptied before data stream 2 can begin transfer. Such a buffer may require a significant amount of memory to accommodate large differences in compression rates.

Alternatively, both bytes from each data stream may be transferred and stored as soon as either of the bytes is full. Each time either data stream 1 or data stream 2 produces a byte's worth of data, the data from both streams is transferred. This sometimes results in one full byte's worth of data and another byte which is not full, which is not efficient. Furthermore, the resources required to transfer two bytes of data are still being used even though less than two bytes are being transferred.

Another option is to transfer each byte from each data stream separately. For example, data stream 1 is transferred to a DMA unit from one "end" of the unit and data stream 2 is transferred to the same unit from another "end" of the unit until the two streams meet, not necessarily in the middle. This takes up two times the resources (e.g. DMA units or processor time) required to effect a transfer and also consumes more current due to more data bus traffic.

Thus, a need exists in the medical arts for transferring and storing data in an implantable medical device.

Several methods have been proposed in the prior art for improving storage and compression in an implantable medical device.

For example, U.S. Pat. No. 5,603,331 to Heemels et al., entitled "Data Logging System For Implantable Cardiac Device" discloses the compression of heart rate variability data via logarithmic data compression and the storing of the results as time-related histograms with a standard deviation.

U.S. Pat. No. 5,819,740 to Muhlenberg entitled "System and Method for Compressing Digitalized Signals in Implantable and Battery-Powered Devices" discloses the compression of data using non-linear sampling. A time varying threshold is used and the signal of interest is compared to the threshold.

U.S. Pat. No. 5,836,982 to Muhlenberg et al., entitled "System and Method of Data Compression and Non-Linear Sampling from Implantable and Battery-Powered Devices" discloses compressing a data block by storing the change, or delta, from one sample to another sample.

U.S. Pat. No. 5,312,446 to Holschbach et al., entitled "Compressed Storage of Data in Cardiac Peacemakers" discloses compression of data using an analog implementation of a turning point algorithm.

U.S. Pat. No. 5,623,935 to Faisandier entitled "Data Compression Methods and Apparatus for Use with Physiological Data" discloses compression of data by generating the first and second derivatives of an analog signal. The first and second derivatives of an analog signal are generated and one of three modes of encoding is selected. Either one of the derivative values is then encoded using one of the three modes based upon maximum compression.

U.S. Pat. No. 5,709,216 to Woodson entitled "Data Reduction of Sensed Values in an Implantable Medical Device Through the Use of a Variable Resolution Technique" discloses compression of data using variable resolution. The variable resolution is based upon pre-selected sub-ranges, i.e., smaller values or intervals have finer resolutions.

U.S. Pat. No. 5,215,098 to Steinhause et al., entitled "Data Compression of Cardiac Electrical Signals Using Scanning Correlation and Temporal Data Compression" discloses data compression by storing pre-recorded (i.e. learned) signal templates.

U.S. Pat. No. 5,217,021 to Steinhause et al., entitled "Detection of Cardiac Arrhythmias Using Correlation of a Cardiac Electrical Signal and Temporal Data Compression" also discloses data compression using stored pre-recorded signal templates.

U.S. Pat. No. 5,836,889 to Wyborny et al., entitled "Method and Apparatus for Storing Signals in an Implantable Medical Device" discloses compression of data for storing a straight-line connection between the last stored value and new data. Data is stored when the first derivative exceeds a threshold.

U.S. Pat. No. 4,716,903 to Hanson et al., entitled "Storage in a Pacemaker Memory" discloses data compression by storing the time to the next sample. The time is stored when the samples are near the baseline. An additional flag is added for turning points.

U.S. Pat. No. 5,263,486 to Jeffreys entitled "Apparatus and Method for Electrocardiogram Data Compression" discloses data compression by varying the sampling period dynamically. The variation is based upon signal rate of change value.

U.S. Pat. No. 4,920,489 to Hubelbank et al., entitled "Apparatus and Method for Solid State Storage of Episodic Signals" discloses compression of data by storing the derivative value, which is defined as data differing from the last stored value. The resolution is also changed based upon the magnitude of rate change.

U.S. Pat. No. 5,735,285 to Albert et al., entitled "Method and Hand-Held Apparatus for Demodulating and Viewing Frequency Modulated Biomedical Signals" discloses transmission of data using A-Law encoding and decoding.

U.S. Pat. No. 5,694,356 to Wong et al., entitled "High Resolution Analog Storage EPROM and Flash EPROM" discloses compression of a signal using A-Law or U-Law log arrhythmic relationships.

As discussed above, the most pertinent prior art patents are shown in the following table:

TABLE 1

Prior Art Patents.

| Patent No. | Date | Inventor(s) |
| --- | --- | --- |
| 5,836,982 | Nov. 17, 1998 | Muhlenberg et al. |
| 5,836,889 | Nov. 17, 1998 | Wyborney et al. |
| 5,819,740 | Oct. 13, 1998 | Muhlenberg |
| 5,735,285 | Apr. 7, 1998 | Albert et al. |
| 5,709,216 | Jan. 20, 1998 | Woodson, III |
| 5,694,356 | Dec. 2, 1997 | Wang et al. |
| 5,623,935 | Apr. 29, 1997 | Faisandier |
| 5,603,331 | Feb. 18, 1997 | Heemels et al. |
| 5,312,446 | May 17, 1994 | Holschbach et al. |
| 5,263,486 | Nov. 23, 1993 | Jeffreys |
| 5,217,021 | Jun. 8, 1993 | Steinhaus et al. |
| 5,215,098 | Jun. 1, 1993 | Steinhaus et al. |
| 4,920,489 | Apr. 24, 1990 | Hubelbank et al. |
| 4,716,903 | Jan. 5, 1988 | Hansen et al. |

All the patents listed in Table 1 are hereby incorporated by reference herein in their respective entireties. As those of ordinary skill in the art will appreciate readily upon reading the Summary of the Invention, the Detailed Description of the Preferred Embodiments and the claims set forth below, many of the devices and methods disclosed in the patents of Table 1 may be modified advantageously by using the teachings of the present invention.

SUMMARY OF THE INVENTION

The present invention is therefore directed to providing a method and system for transferring and storing data in an implantable medical device, such as a cardiac pacing device. The system of the present invention may overcome at least some of the problems, disadvantages and limitations of the prior art described above, and provides a more efficient and accurate means of transferring and storing data, such as heart signal data, in an implantable medical device.

The present invention has certain objects. That is, various embodiments of the present invention provide solutions to one or more problems existing in the prior art respecting the pacing of cardiac tissue. Those problems include, without limitation: (a) limited data storage capacity of an implantable device; (b) limited data processing capabilities of an implantable device; (c) variability in data stream rates for data being stored in an implantable medical device; (d) variability in data stream rates for data being compressed or otherwise processed by an implantable medical device; and (e) difficulty in identifying one data stream being processed and/or stored in an implantable medical device from another data stream being processed and/or stored.

In comparison to known techniques for storing data in an implantable device, various embodiments of the present invention may provide one or more of the following advantages: (a) increased data storage capacity in an implantable device; (b) the ability to more efficiently process variable rate data streams in an implantable device; (c) the ability to transfer and store variable rate data streams in an implantable device; (d) the ability to distinguish one data stream being compressed or otherwise processed from another data stream in an implantable device; and (e) the ability to uniquely identify and store a given data stream in an implantable device.

Some of the embodiments of the present invention include one or more of the following features: (a) an implantable device with increased data storage capacity; (b) an implantable device capable of transferring and storing variable rate data streams; (c) an implantable device capable of distinguishing between two or more data streams that have been compressed or otherwise processed; (d) methods of transferring compressed data from one or more data streams with variable rates and (e) methods of distinguishing one data stream from another in an device with limited memory.

At least some embodiments of the present invention involve collecting first data stream data into a first intermediate register while additional data stream data is collected into an additional intermediate register. First intermediate register contents are stored in at least one first output register. Additional intermediate register contents may also be stored in the first output register. First intermediate register contents or additional intermediate register contents may also be stored in at least one additional output register. Alternatively, first intermediate register contents or additional intermediate register contents may be stored in either the first intermediate register or the additional intermediate register if the additional output register is full. Intermediate register contents may also be stored with an identification code that uniquely identifies each data stream from another.

BRIEF DESCRIPTION OF THE DRAWINGS

The above, and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PRESENTLY PREFERRED EMBODIMENTS

It is to be understood that the terms "IPG" and "IMD", as employed in the specification and claims hereof, means an implantable medical device capable of delivering electrical stimuli to cardiac tissue, and includes within its scope pacemakers, PCDs, ICDs, etc.

Figure 1:
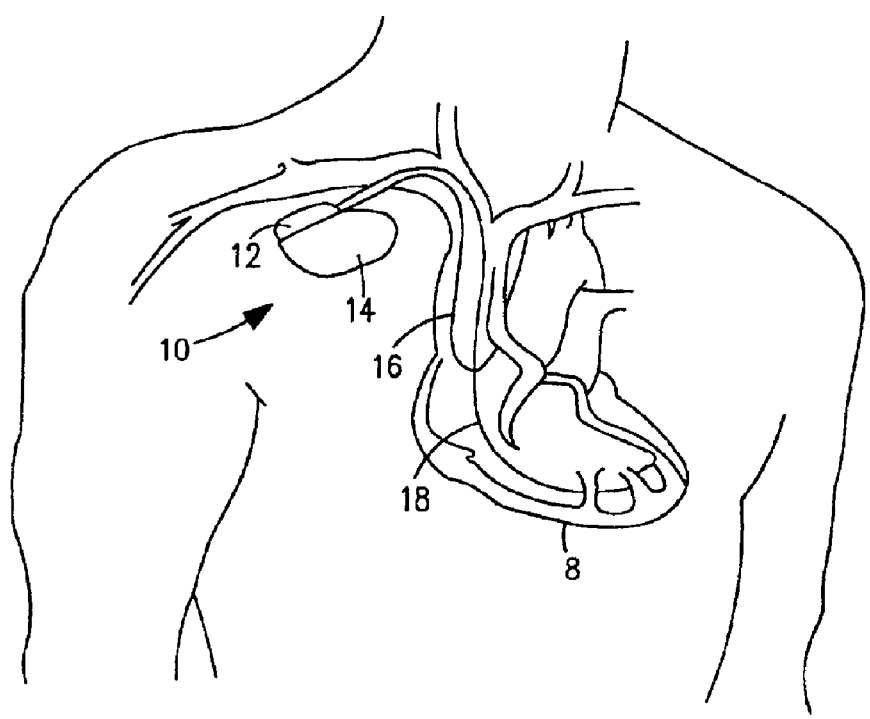
FIG. 1 is a schematic view of one embodiment of an implantable medical device in situ, made in accordance with the present invention.

FIG. 1 is a simplified schematic view of one embodiment of implantable medical device ("IMD") 10 of the present invention. The IMD 10 shown in FIG. 1 is a pacemaker comprising at least one of pacing and sensing leads 16 and 18. Leads 16, 18 may be attached to hermetically sealed enclosure 14 and may be implanted near heart 8. Pacing lead 16 and sensing lead 18 may sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all of which are hereby incorporated by reference, each in their respective entireties.

Figure 2:
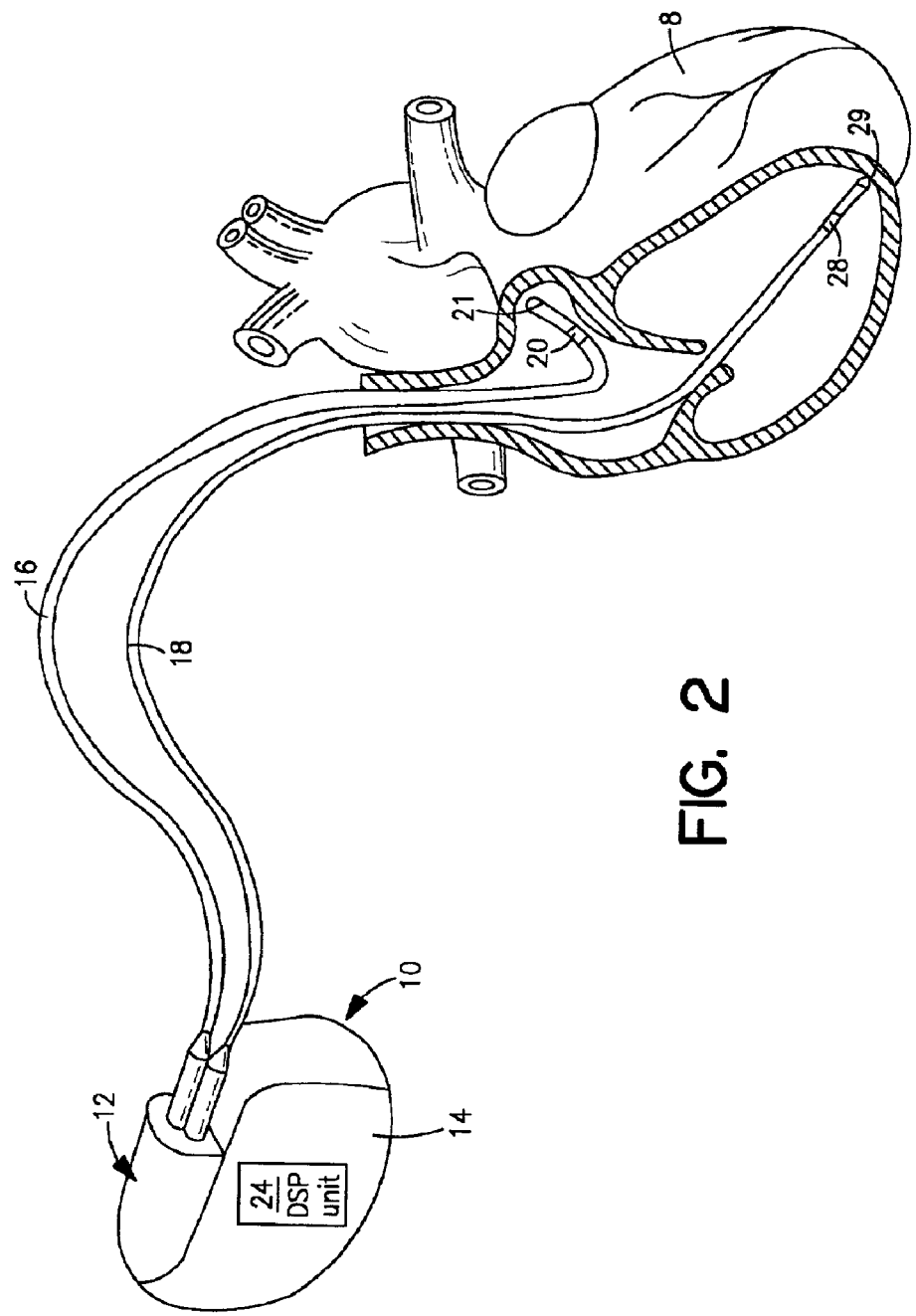
FIG. 2 is another schematic view of an embodiment of the implantable medical device of FIG. 1, made in accordance with the present invention.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle. As seen in FIG. 2, IMD 10 may also include or be in communication with a digital signal processing (DSP) unit 24.

Figure 3:
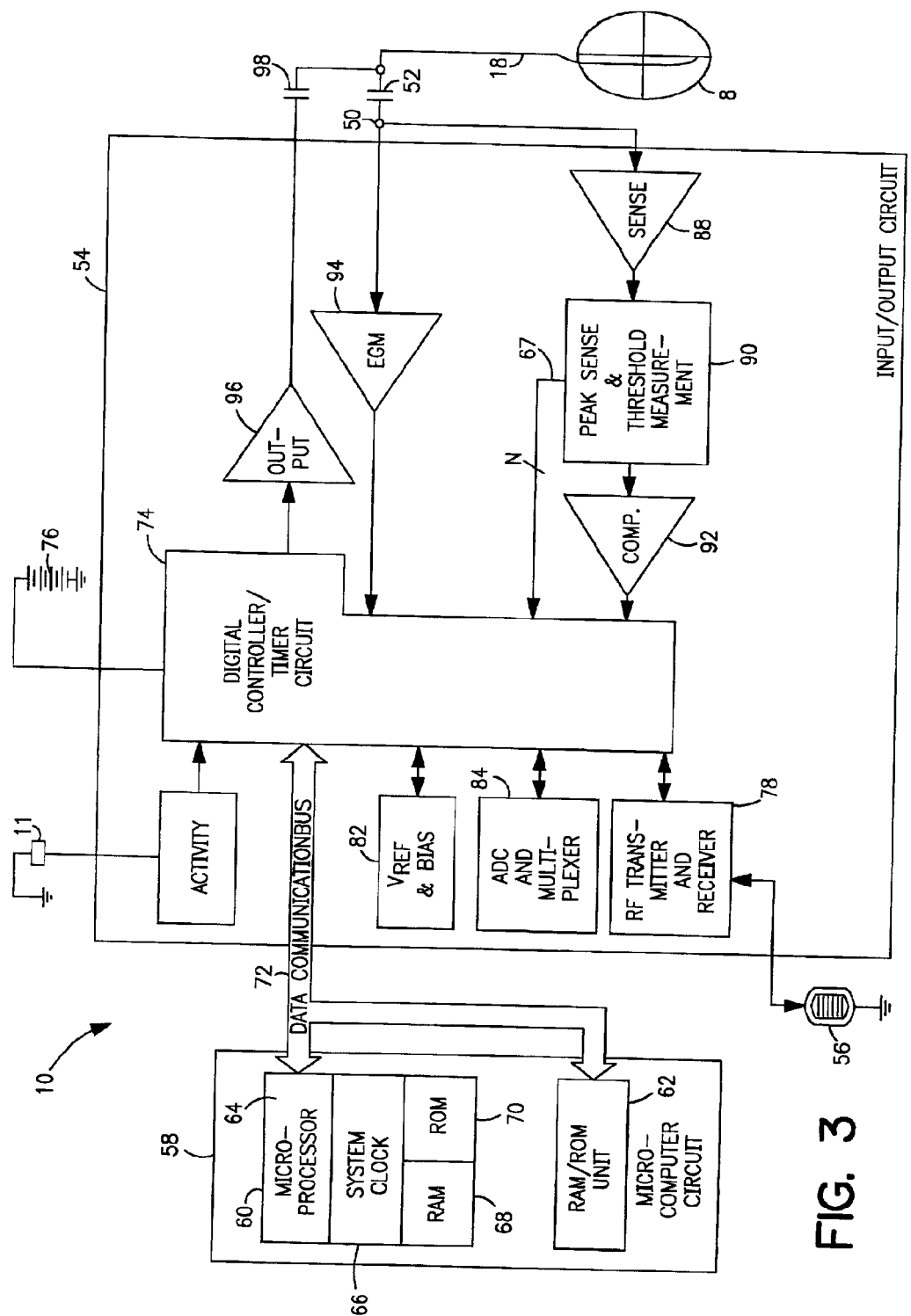
FIG. 3 is a block diagram illustrating components of an embodiment of the implantable medical device of FIG. 1, made in accordance with the present invention.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor 11. Activity sensor 11 may be, for example, an accelerometer based on silicon technology, a piezoceramic accelerometer or an accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference in its entirety. The programming methodology disclosed in the '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 may be controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 may be powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063, issued to Thompson et al. and hereby incorporated by reference in its entirety, or to that disclosed in the above-referenced '453 patent. In one embodiment of the invention, the particular programming and telemetry scheme selected permits the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and bias circuit 82 most preferably generate stable voltage reference and bias currents for analog circuits included in input/output circuit 54. Analog-to-digital converter (ADC) and multiplexer unit 84 digitizes analog signals and voltages to provide "real-time" telemetry intracardiac signals, storage of intracardiac signals and battery end-of-life (EOL) replacement functions. Operating commands for controlling the timing of IMD 10 are coupled by data communication bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD and DDI, modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is further not limited to IMDs comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMDs. See, for example, U.S. Pat. No. 5,800,465 to Thompson et al., hereby incorporated by reference herein in its entirety, as are all U.S. patents referenced therein.

IMD 10 may also be a pacemaker-cardioverter-defibrillator ("PCD") corresponding to any of numerous commercially available implantable PCDs. Various embodiments of the present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all of which are hereby incorporated by reference, each in their respective entireties.

Figure 4:
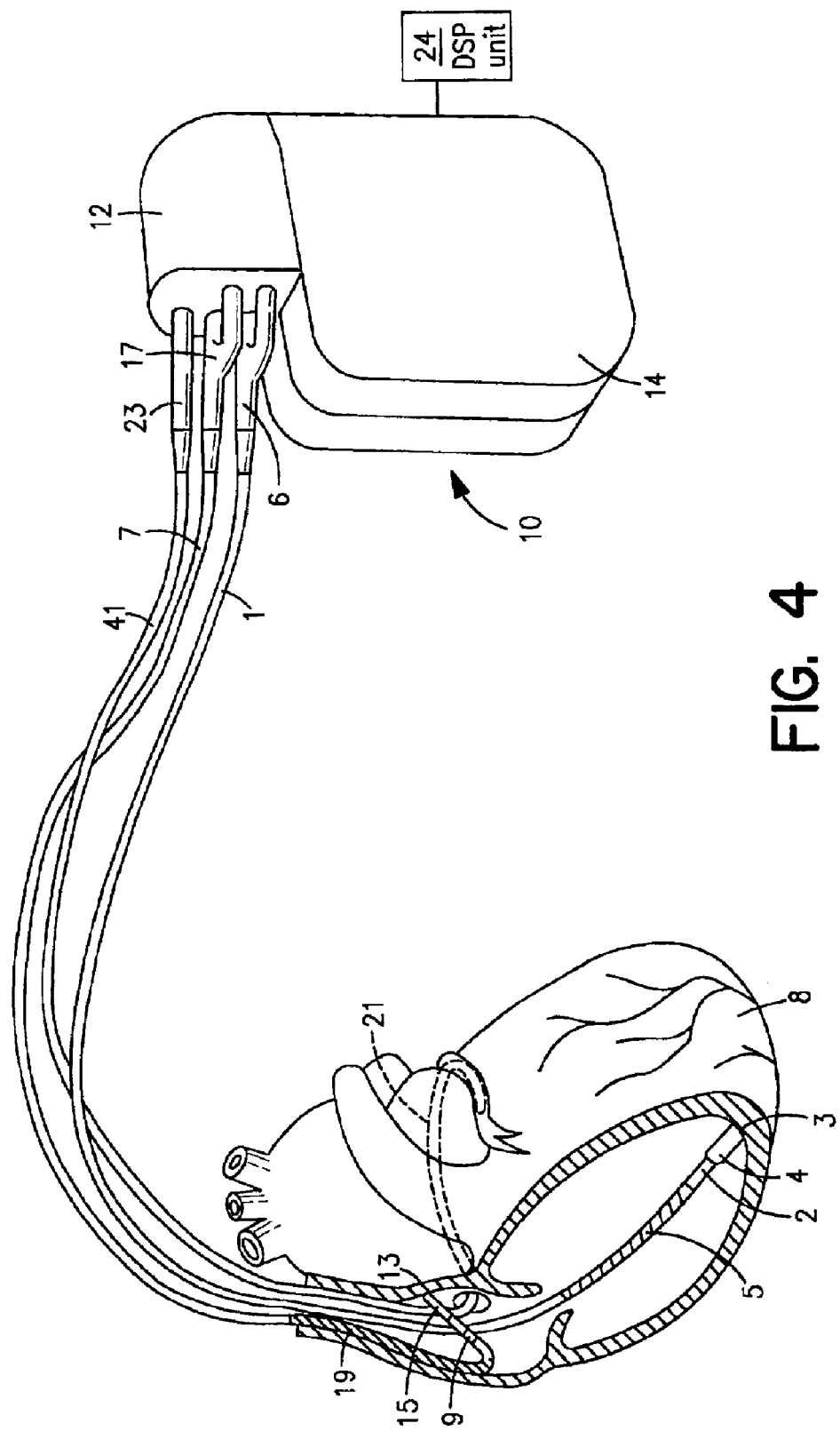
FIG. 4 is a schematic view of another embodiment of an implantable medical device, made in accordance with the present invention.
Figure 5:
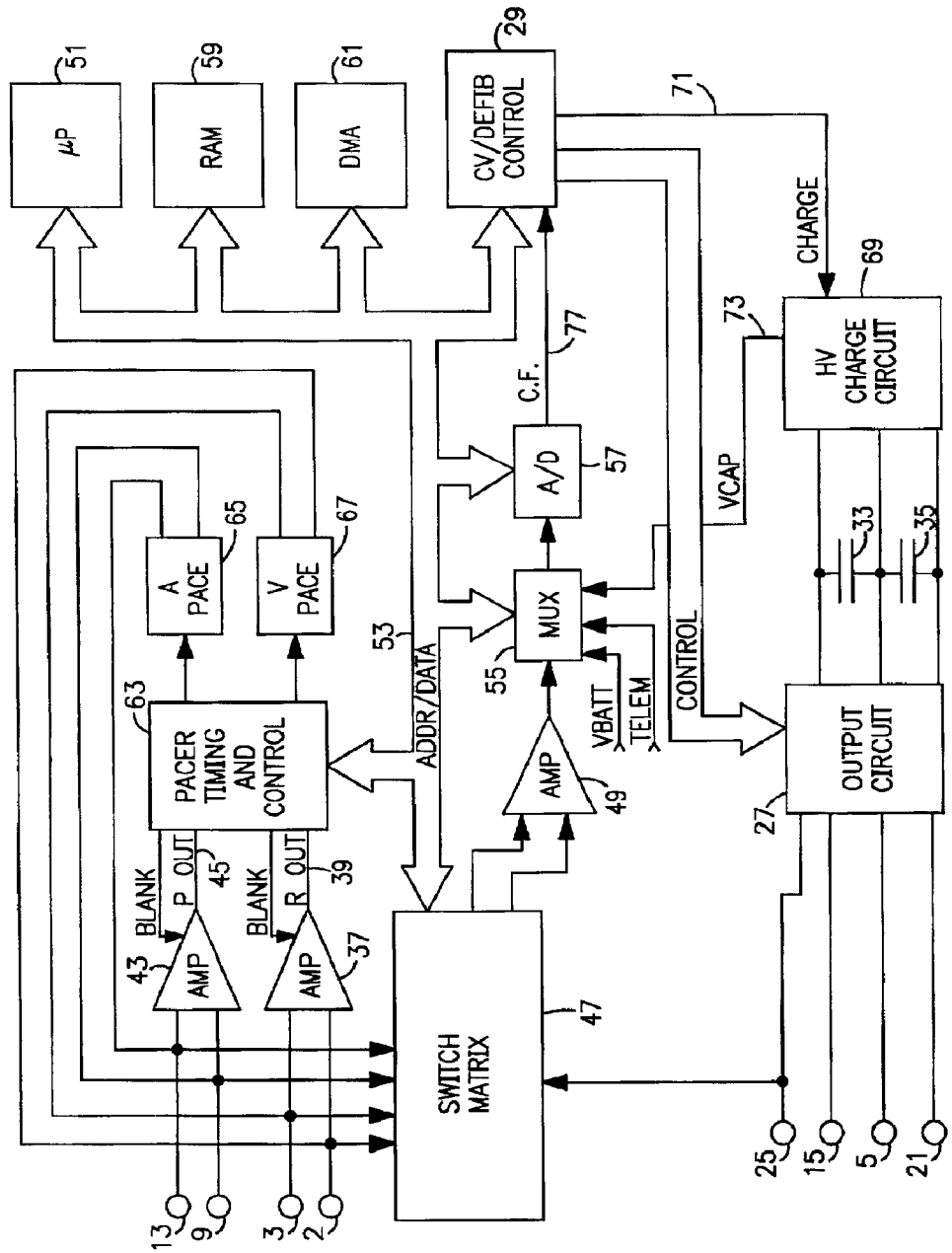
FIG. 5 is a block diagram illustrating components of an embodiment of the implantable medical device of FIG. 4, made in accordance with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in the '838 and '430 patents, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6, which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17, which carries three electrical connectors, each coupled to one of the coiled conductors.

The coronary sinus lead shown in FIG. 4 assumes the form of a coronary sinus lead disclosed in the above cited '838 patent, and includes elongated insulative lead body 41 carrying one coiled conductor coupled to an elongated coiled defibrillation electrode 21. Electrode 21, illustrated in broken outline in FIG. 4, is located within the coronary sinus and the great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillate electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference in its entirety. As seen in FIG. 4, PCD 10 may also include or be in communication with a digital signal processing (DSP) unit 24.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

PCD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals," hereby incorporated by reference in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in RAM (memory) 59 under control of direct memory access circuit 61. Microprocessor 51 may employ digital signal analysis techniques to characterize the digitized signals stored in RAM (memory) 59 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention, may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in RAM (memory) 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on the generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R—R intervals, P—P intervals, P–R intervals and R–P intervals, which measurements are stored in RAM (memory) 59 and used to detect the presence of tachyarrhythmias.

Microprocessor 51 most preferably operates as an interrupt driven device, and is responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to any of the various tachyarrhythmia detection algorithms presently known in the art. For example, the presence of an atrial or ventricular tachyarrhythmia may be confirmed by detecting a sustained series of short R—R or P—P intervals of an average rate indicative of tachyarrhythmia or an unbroken series of short R—R or P—P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005, issued to Pless et al. and U.S. Pat. No. 4,830,006, issued to Haluska et al., all hereby incorporated by reference, each in their respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pp. 167–170, also hereby incorporated by reference in its entirety. Atrial fibrillation detection methodologies are disclosed in published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are hereby incorporated by reference in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are hereby incorporated by reference in their entireties, may also be employed.

In the event that the generation of a cardioversion or defibrillation pulse is required, microprocessor 51 may employ an escape interval counter to control timing of such cardioversion and defibrillation pulses, as well as the associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy, microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., all of which are hereby incorporated by reference, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all of which are hereby incorporated by reference in their entireties, may also be employed.

Continuing to refer to FIG. 5, delivery of cardioversion or defibrillation pulses may be accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches, which control whether electrodes are coupled together during delivery of the pulse. Alternatively, electrodes intended to be coupled together during the pulse may simply be permanently coupled to one another, either exterior to or within the interior of the device housing, and polarity may similarly be pre-set, as in current implantable defibrillators. An example of output circuitry for delivery of biphasic pulse regimens to multiple electrode systems may be found in U.S. Pat. No. 4,953,551, issued to Mehra, and in U.S. Pat. No. 4,727,877, both of which are hereby incorporated by reference in their entireties.

An example of circuitry that may be used to control delivery of monophasic pulses is disclosed in U.S. Pat. No. 5,163,427 to Keimel, also hereby incorporated by reference in its entirety. Output control circuitry similar to that disclosed in the '551 patent or in U.S. Pat. No. 4,800,883 to Winstrom, which is hereby incorporated by reference in its entirety, may also be used in conjunction with various embodiments of the present invention to deliver biphasic pulses.

Alternatively, IMD 10 may be an implantable nerve stimulator or muscle stimulator, such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference, each in their respective entireties. The present invention is believed to find wide application to any form of implantable electrical device for use in conjunction with electrical leads.

In one embodiment of the invention, IMD 10 may also be, for example, an implantable medical device containing a Digital Signal Processing (DSP) unit 24 as seen above. Alternatively, IMD 10 may be any medical device with restricted volume, with restricted power supply, with restricted storage capacity or having a combination of these restrictions.

Figure 6:
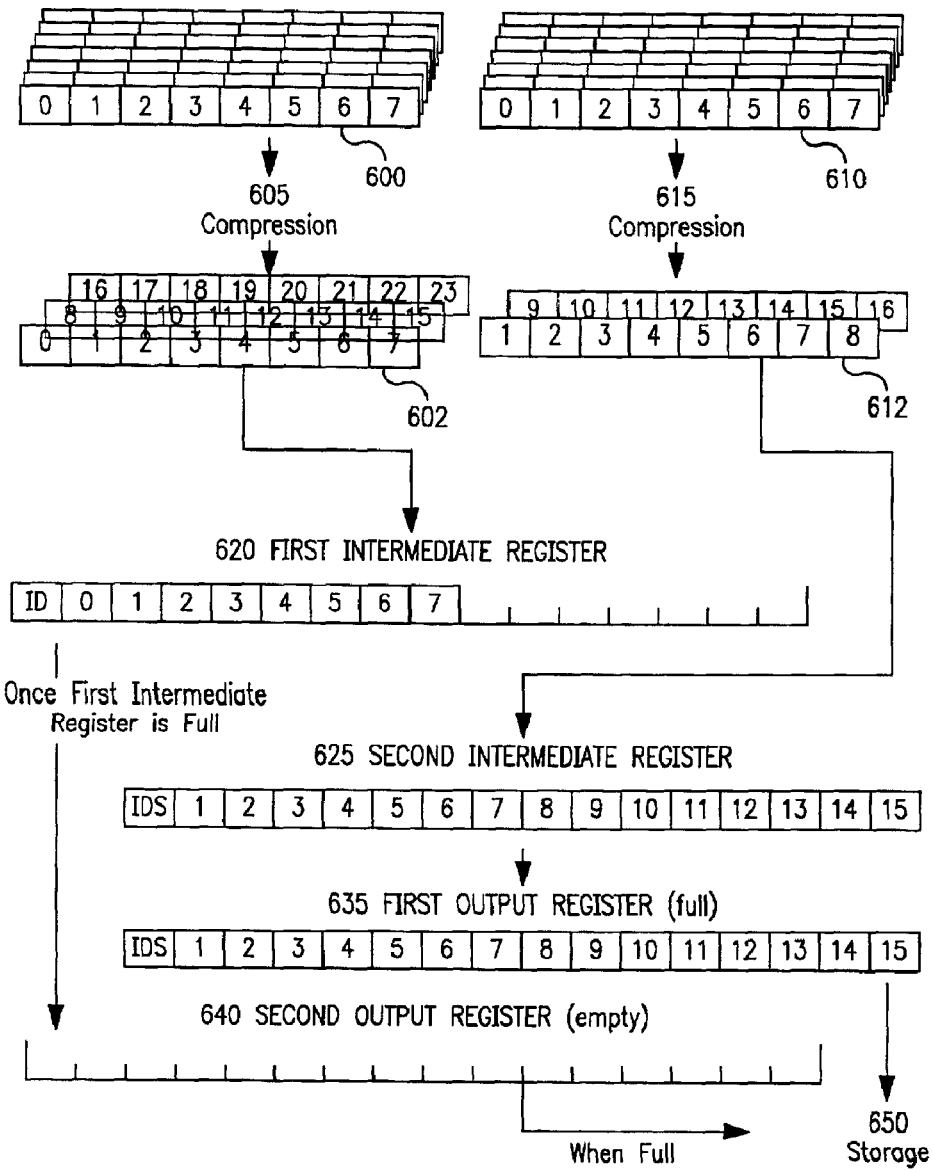
FIG. 6 is a schematic representation of two data streams processed in accordance with one embodiment of the present invention.

FIG. 6 shows a schematic representation of two data streams being processed in accordance with the present invention at 600 and 610. Alternatively, any suitable number of data streams may be combined. For example, four data streams may be combined or eight data streams may be combined.

In one embodiment of the invention, the data streams to be combined are two parallel digital data streams. Each data stream may represent one cardiac signal or a processed version of a cardiac signal. For example, the data streams may represent cardiac signals received from sensing leads 16, 18 or may represent data from pacing signals administered by pacing leads or electrodes as described above. The data streams may be generated by any suitable means such as, for example, the circuitry of device 10, including but not limited to sensing circuitry, measurement circuitry 90, pacer timing/control circuitry 63 pacer output circuitry 65 and 67, or cardioversion/defibrillation control circuitry 29. The data streams may also be generated or otherwise processed by microprocessor 64. The data streams may be stored or otherwise processed in RAM 68 and ROM 70. In one embodiment of the invention, the data streams are generated or otherwise processed by a digital signal processor 24 as described above.

In the embodiment shown in FIG. 6, the data streams 600, 610 are not compressed and have the same fixed width and fixed sample rate. In one embodiment of the invention, data stream 600 comprises a plurality of data bits. Data stream 610 may also comprise a plurality of data bits.

The data streams 600, 610 may then undergo processing. For example, data streams 600, 610 may undergo any suitable method of processing which results in output data streams that have variable data rates or variable data widths. For example, the data streams may be multi-bit digital signals processed by A/D converter 57, for storage in RAM (memory) 59 under control of direct memory access circuit 61.

In one embodiment of the invention, data streams 600, 610 are processed by compression as indicated at 605, 615. Compression at 605, 615 may be accomplished using any suitable compression algorithm, for example, a compression algorithm that compresses 8-bit values into variable size and sample rate data. Alternatively, the compression algorithm may process other sized bit values, including, but not limited to, 6-bit, 10-bit, 16-bit or 32-bit values into variable size and sample rate data. One compression algorithm that may be used in accordance with the present invention is described in co-pending U.S. patent application Ser. No. 09/847,049.

After processing, output data streams may be produced. Each of these output data streams may correspond to an original data stream before processing. For example, output data streams 602, 612 of FIG. 6 correspond to data streams 600, 610 respectively. After processing, data stream 602 may typically have a size and/or sample rate which differs from the size and/or sample rate of data stream 612.

Components (e.g. bits) of first data stream 602 may now be stored in first intermediate register 620. First intermediate register 620 may be any suitable component of IMD 10 for collecting and/or storing data. For example, first intermediate register 620 may be a hardware component for storage of data. Alternatively, first intermediate register 620 may be a storage location of IMD 10, including but not limited to, a location of memory 59, RAM 68 or ROM 70. In one embodiment of the invention, intermediate register 620 consists of a data portion and an identification code ID which resides at a known location, for example, a known location within the register, including, but not limited to the first location in the register 620. The identification code ID occupies the minimum number of bits that is sufficient to uniquely identify every data stream that is to be transported and stored. For identification of one data stream out of two, a single bit may suffice as identification code ID. Alternatively identification code ID may be any suitable bit size, including but not limited to 2-bit, 6-bit, 10-bit, 16-bit or 32-bit.

In the embodiment shown in FIG. 6, first intermediate register 620 has a size of 16, of which 15 bits are designated as data bits and one bit is designated as a location for an identification code ID. This means that the first intermediate register of FIG. 6 may collect data from first data stream 602 until it has collected 15 bits. Alternatively, first intermediate register 620 may have any suitable size including but not limited to 2-bit, 6-bit, 8-bit, 10-bit, or 32-bit. In the example of FIG. 6, first intermediate register 620 will collect these first 15 bits from a 16-bit data stream 602. Then the identification code ID, that identifies data stream 602 is stored in a known location of first intermediate register 620. In the embodiment shown in FIG. 6, the identification code ID is stored in the first bit location of first intermediate register 620 to fill register 620. Continuing the above example, the identification code ID of data stream 602 may be a zero (0) stored in the first bit location of the register 620. Although FIG. 6 shows the identification code ID at the front of first intermediate register 620, it may be located in any suitable location of first intermediate register 620. Moreover, although the identification code ID of data stream 602 is a single zero (0) filling a single bit in the embodiment of FIG. 6, identification code ID may be any suitable symbol filling any suitable number of bits.

In one embodiment of the invention, first intermediate register 620 may be filled with data without the immediate addition of identification code ID. Identification code ID may then be attached later, for example, when the contents of first intermediate register 620 are being transferred to an output register. This may reduce the necessity of moving data from an intermediate register that may be predicted or attached at the output register. Alternatively, identification code ID may be moved into first intermediate register 620 before it is filled.

In the meantime, components (e.g. bits) of second data stream 612 may be synchronously collected in second intermediate register 625. Second intermediate register 625 may be any suitable component of IMD 10 for collecting and/or storing data. For example, second intermediate register 625 may be a hardware component for storage of data. Alternatively, second intermediate register 625 may be a storage location of IMD 10, including but not limited to a location of memory 59, RAM 68 or ROM 70. In one embodiment of the invention, second intermediate register 625 consists of a data portion and an identification code ID5. For the purposes of this invention, reference numerals ID and ID5 may both be described as at least one bit in a particular register that is used to uniquely identify a data stream. That is, the identification code associated with a data stream uniquely identifies that stream. For example, identification code ID may be associated with data stream 602 whereas identification code ID5 may be associated with data stream 612. These identification codes may reside at a known location. The identification code ID, ID5 may preferably occupy the minimum number of bits that is sufficient to uniquely identify every data stream that is to be transported and stored. For identification of one data stream out of two, a single bit may suffice as identification code ID5. Alternatively, to identify one data stream out of several data streams, more than one bit may be used as identification code ID, ID5.

In the embodiment shown in FIG. 6, second intermediate register 625 has the same size as first intermediate register 620, i.e., 16. Alternatively, second intermediate register 625 may have a size differing from that of first intermediate register 620. Second intermediate register 625 may be any suitable size, including, but not limited to 2-bit, 6-bit, 8-bit, 10-bit or 32-bit. With a size of 16, 15 bits may be designated as data bits and one bit may be designated as a location for an identification code ID5. Thus, the second intermediate register 625 of FIG. 6 may collect data from second data stream 612 until it has collected 15 bits. Then the identification code ID5, that identifies data stream 612 is stored in second intermediate register 625 to fill register 625. Continuing the above example, the identification code ID5 of data stream 612 may be a one (1) stored in the ID code location of second intermediate register 625. Moreover, although the identification code ID5 of data stream 612 is a single one (1) filling a single bit in the embodiment of FIG. 6, identification code ID5 may be any suitable symbol filling any suitable number of bits.

First intermediate register 620 and second intermediate register 625 may fill at different rates. The difference in rates may be due to a difference in the rate of compression of the two streams. Alternatively, the difference in rates may be due to different input sample rates. Alternatively, the difference in rates may be due to data streams that have input sample rates that change depending on the sample data.

For example, in the embodiment shown in FIG. 6, second intermediate register 625 fills more quickly than first intermediate register 620.

Once either of the intermediate registers 620, 625 is full, the contents of the full intermediate register may be transferred to an output register 635, 640. Output register 635, 640 may be any suitable component of IMD 10 for storing data. Output register 635, 640 may be the same or different in size from one or both of the intermediate registers. In one embodiment of the invention, intermediate registers 620, 625 and output registers 635, 640 are all the same size. Alternatively, output register 635, 640 may be of such a size that the contents of intermediate registers 620, 625 may be combined into the output register before storage. For example, intermediate registers 620, 625 may both have a size of 8 and output register 635 may have a size of 16 or intermediate registers 620, 625 may both have a size of 16 and output register 635 may have a size of 32. In cases of combined contents, time of availability of data bytes in streams 602, 612, as described further below, may be used to determine whether two portions of stream 602, two portions of stream 612 or a portion from each stream 602, 612 may be combined to fill output register 635, 640.

In the embodiment shown in FIG. 6, second intermediate register 625 is filled before first intermediate register 620. So the contents of intermediate register 625 are transferred to an empty first output register 635, which then becomes full. As seen at 650, once first output register 635 is full, its contents may be transported and stored.

Meanwhile, second output register 640 may be available for filling. Depending on the compression algorithm, second intermediate register 625 may be filled again before first intermediate register 620 is filled. Thus, again, the contents of second intermediate register 625 are transferred to an output register. In one embodiment of the invention, the contents of second intermediate register 625 are transferred to second output register 640, which is empty while first output register 635 is still full. Thus, first output register 635 or second output register 640 may be filled in any suitable sequence in accordance with the present invention depending on their respective states of full or empty. Then, when either output register is full, its contents may be transferred to storage at 650.

To continue with the above example, the first fraction of 15 bits of first data stream 602 now finishes filling first intermediate register 620. Meanwhile, the third fraction of 15 bits of second data stream 612 are still being collected into second intermediate register 625. First intermediate register contents are then transferred to any empty output register, in this case first output register 635. From there, first output register 635 contents are again transferred to storage at 650.

Then, the third fraction of 15 bits of second data stream 612 fills second intermediate register while first data stream 602 begins the process of filling first intermediate register 620 again. This third fraction of 15 bits (and ID) from data stream 612 are transferred to any empty output register, in this case, second output register 640, which is again empty. From there, first output register 635 contents are again transferred to storage at 650. Meanwhile, second intermediate register 625 may fill with a fourth fraction of 15 bits (and ID) to be transferred to first output register 635 and subsequently transferred to storage. Continuing with the above example, first data stream 602 again fills its first intermediate register 620 in time to transport its first intermediate register contents to the second output register 640 which is again empty. In this example, second data stream 612 may now produce data at a slower rate than first data stream 602. So first data stream 602 may alternately fill output registers 635, 640 from its first intermediate register 620 for a time while second data stream 612 takes a longer time to fill its second intermediate register 625. Thus, first data stream 602 produces another fraction of 15 bits to fill first intermediate register 620 and subsequently first output register 635, which is again empty. As seen from this example, data streams 602, 612 may fill their respective intermediate registers 620, 625 at any suitable rate. Alternatively, in one embodiment of the invention, the data streams 602, 612 may fill intermediate registers 620, 625 at similar rates.

Because of the use of identification, such as identification codes ID, ID5, the data streams transported from one or both output registers 635, 640 are still identifiable. Continuing the above example, the data streams stored above may look like a sequential row of 16-bit storage locations, wherein each 16-bit location can be identified as belonging to either data stream 602 or data stream 612 via one or more identification codes as described above. For example if zero (0) is used to identify first data stream 602 and one (1) is used to identify second data stream 612, the following 16-bit locations can be identified as belonging to one or the other of data streams 602, 612:

1010101011101110 (data stream 612)
1101010101110111 (data stream 612)
0010101010111011 (data stream 602)
1101010101011101 (data stream 612)
1010101011101111 (data stream 612)
0011111110111110 (data stream 602)
0001101001111101 (data stream 602)

As a further example, two data streams may again be designated 602 and 612. In one embodiment of the invention, samples may be collected in first intermediate register 620 until 7 bits of data are full. If an output register 635 is empty, the 8 bits (identification code ID plus 7 data bits) may be transported to an output register and the remaining bits may be stored in first intermediate register 620. If output register 635 is filled already but output register 640 is empty, the 8 bits may be transported to output register 640 (and extra bits may be stored in first intermediate register 620). Simultaneously, the same may be done with data stream 612 samples, using second intermediate register 625 instead of first intermediate register 620, but still trying first output register 635 first and then second output register 640,. As soon as first output register 635 and second output register 640 are both filled, an interrupt may be generated, such as for example a DMA interrupt. After DMA has read the output word from first output register 635 and second output register 640, output registers 635, 640 may then be marked empty again.

In another example, if the data streams 602, 612 produce data at the same rate, first intermediate register 620 and second intermediate register 625 will be full at the same sample. First contents of first intermediate register 620 will be transferred to first output register 635 and then contents of second intermediate register 625 will be transferred to second output register 640 (provided that both output registers 635, 640 were empty). The data may be read from output registers 635, 640. Output registers 635, 640 may then be emptied again and the cycle may be repeated. In case of equal data rates, first data stream data may always go to the same output register and second data stream data may always go to the other output register.

If data streams 602, 612 produce data at different rates, the following may occur. Suppose data stream 602 produces more data, and output registers 635, 640 are both empty. Now samples from data stream 602 may be collected in first intermediate register 620 until 7 bits are full. The contents of first intermediate register 620 may be transferred to first output register 635. Samples from data stream 602 may continue coming until first intermediate register 620 is full again. The contents of first intermediate register 620 may then be transferred to second output register 640. An interrupt may then generated. Data from output registers 635, 640 may then be stored in RAM. Output registers 635, 640 may now be empty. When data stream 612 produces enough data to fill second intermediate register 625, the data may be transferred to first output register 635 if it is empty or to second output register 640 if first output register 635 is full. Data from data streams 602, 612 may then be combined at byte-level after they have been taken from output registers 635, 640 and stored in RAM. Identification codes ID, ID5 may then be used to indicate whether the data originally came from data stream 602 or 612.

A slightly more complicated scenario is when first data stream 602 produces more data than second data stream 612, and first output register 635 is full and second output register 640 is empty. Now suppose samples from data stream 600 are collected in first intermediate register 620 until it is full, and second intermediate register 625 happens to be full at the same time. Then the contents of first intermediate register 620 may be transferred to second output register 640 and an interrupt is given. The transfer of the contents of second intermediate register 625 may then be delayed until the output word of output registers 635, 640 and the output registers 635, 640 have been emptied.

Figure 7:
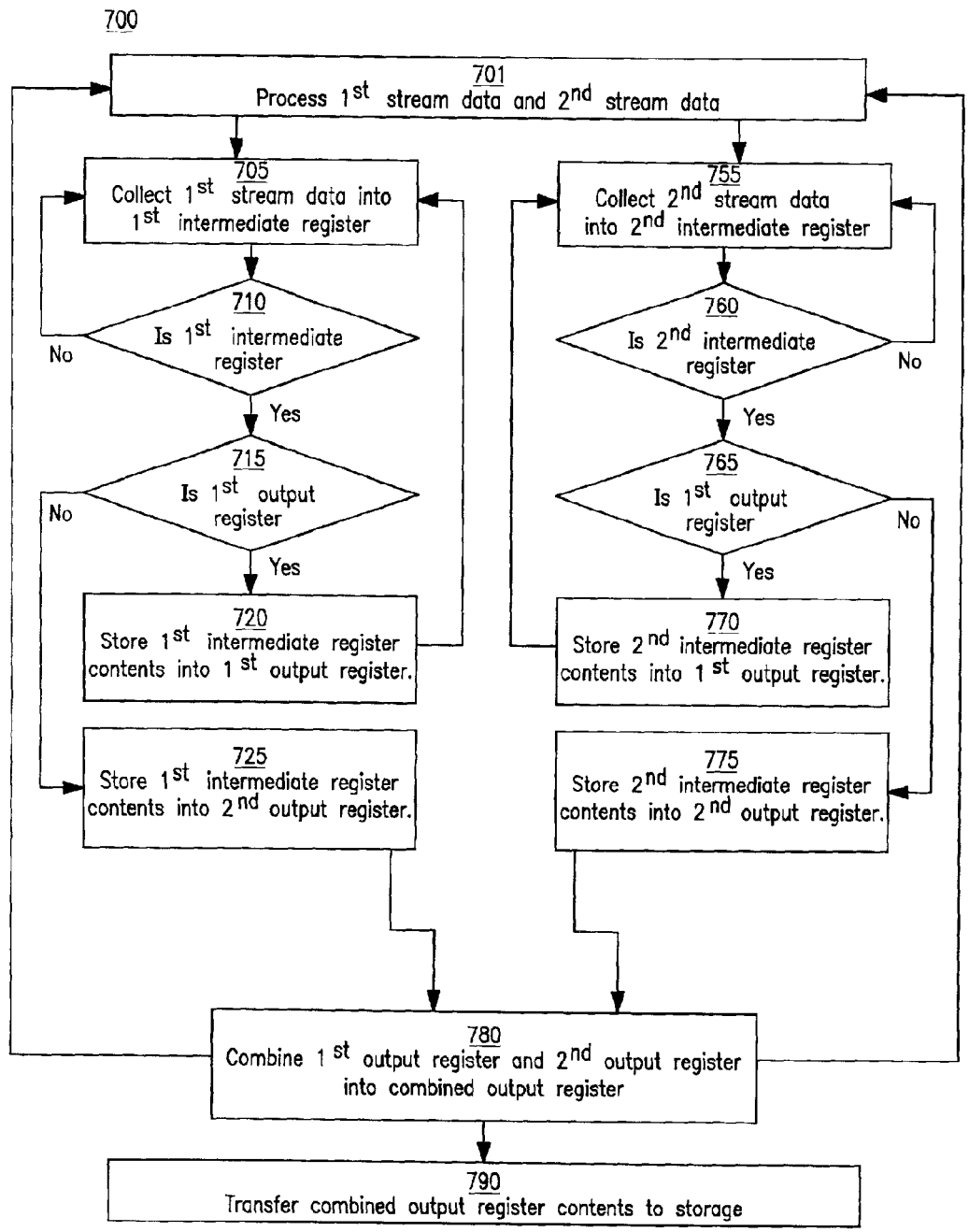
FIG. 7 is a flow diagram of one embodiment of a method for transferring compressed data in accordance with the present invention.

FIG. 7 shows one embodiment of a method for transferring compressed data in an implantable medical device in accordance with the present invention at 700. As discussed above, the method of the present invention may be performed under the control of any appropriate computer algorithm stored in a memory or a portion of a memory of microcomputer 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 64/microcomputer 58.

At block 701, a first data stream and a second data stream may be processed. The data streams may be processed in any suitable manner, as described above. For example in one embodiment of the invention, the data streams may be multi-bit digital signals processed by A/D converter 57, for storage in RAM (memory) 59 under control of direct memory access circuit 61. Microprocessor 51 may be employed in accordance with the present invention to compress, collect, analyze and/or otherwise process the data streams. In one embodiment of the invention, the data streams are compressed. For example, the streams may be compressed using a digital signal processing (DSP) unit 24.

At block 705, samples may be collected from the first data stream. Samples may take the form of, for example, an 8-bit sequence of data information as described above. These samples may be collected into a first intermediate register.

At block 710, it may be determined whether or not the first intermediate register is full. In one embodiment of the invention, the first of two intermediate registers has a size of 16 and is considered full when it has received 15 bits of data information and an identification code of one bit as described above. Alternatively, the first of four intermediate registers may have a size of 16 and be considered full when it has received 14 bits of data information and an identification code of two bits. Other permutations are possible in accordance with the present invention. If the first intermediate register is not full, it may continue to receive samples from the data stream as described at block 705 above. In one embodiment of the invention, this determination may be made by microprocessor 51.

As seen at block 715, if the first intermediate register is determined to be full, it may then be determined whether the first output register is empty. If the first output register is empty, all first intermediate data, that is the bit or bits comprising the identification code and any number of other data bits are then moved from the first intermediate register into the first output register, as seen at block 720. In one embodiment of the invention, the bit or bits comprising the identification code and all the other data bits in the first intermediate register are moved to the first output register. For example, if the first intermediate register has a size of 16, 16 bits may be moved to the first output register. Alternatively at block 715, it may be determined that the first output register is not empty. In this case, all first intermediate data, that is the bit or bits comprising the identification code and any number of other data bits, may then be moved from the first intermediate register into the second output register, as seen at block 720. For example, if the first intermediate register has a size of 16, 16 bits may be moved to the second output register.

As seen at block 780, the contents of first and second output registers may be combined before being transferred to storage at block 790. In one embodiment of the invention, the transfer of all output register data to storage (block 790) empties both output registers.

In the meantime, at block 755, samples may be collected from the second data stream. These samples may be collected into a second intermediate register.

At block 760, it may be determined whether or not the second intermediate register is full. If the second intermediate register is not full, it may continue to receive samples from the data stream as described at block 755 above.

As seen at block 765, if the second intermediate register is determined to be full, it may then be determined whether the first output register is empty. If the first output register is empty, all second intermediate data, that is the bit or bits comprising the identification code and any number of other data bits are then moved from the second intermediate register into the first output register, as seen at block 770. Alternatively at block 765, it may be determined that the first output register is not empty. In this case, all second intermediate data may then be moved from the second intermediate register into the second output register, as seen at block 775.

Figure 8:
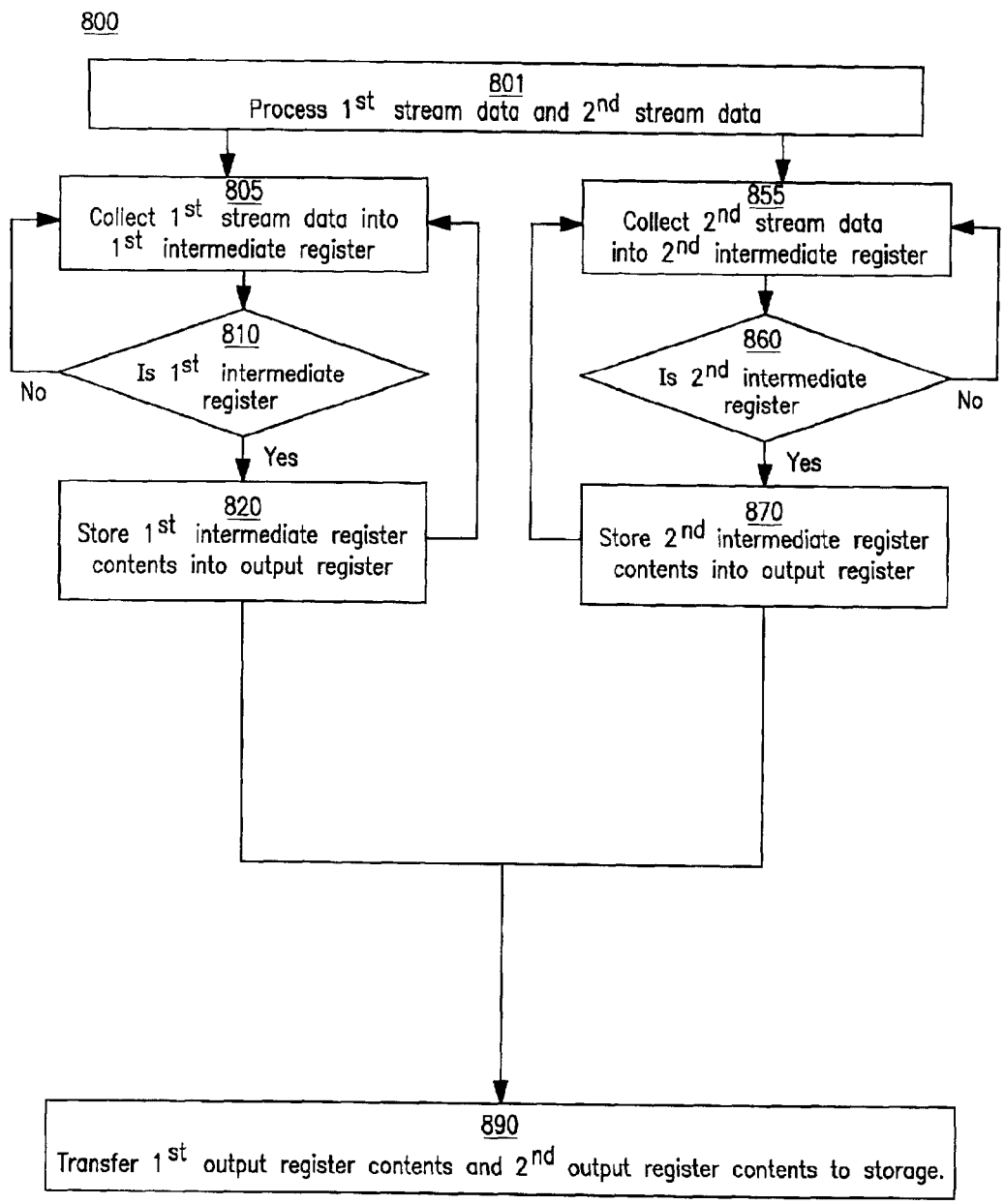
FIG. 8 is a flow diagram of another embodiment of a method for transferring compressed data in accordance with the present invention.

FIG. 8 shows another embodiment of a method for transferring and storing data in accordance with the present invention at 800.

At block 801, a first data stream (for example data stream 600) and a second data stream (for example data stream 610) may be processed. The data streams may be processed in any suitable manner, for example, as described above, via compression. For example in one embodiment of the invention, the data streams may be multi-bit digital signals processed by A/D converter 57, for storage in RAM (memory) 59 under control of direct memory access circuit 61. Microprocessor 51 may be employed in accordance with the present invention to compress, collect, analyze and/or otherwise process the data streams. In one embodiment of the invention, the data streams are compressed. For example, the streams may be compressed using a digital signal processing (DSP) unit 24.

At block 805, samples are collected from the first data stream. Samples may take the form of, for example, an 8-bit sequence of data information as described above. These samples are collected into a first intermediate register.

At block 810, it is determined whether or not the first intermediate register is full. In one embodiment of the invention, the first intermediate register has a size of 16 and is considered full when it has received 15 bits of data information and an identification code of one bit as described above. Alternatively, for transfer and storage of four data streams, the first intermediate register may have a size of 16 and be considered full when it has received 14 bits of data information and an identification code of two bits. Other permutations are possible in accordance with the present invention. If the first intermediate register is not full, it may continue to receive samples from the data stream as described at block 805 above.

As seen at block 820, if the first intermediate register is determined to be full, its contents may be stored in an output register. In one embodiment of the invention, the bit or bits comprising the identification code and all the other data bits in the first intermediate register are moved to an empty output register. For example, if the first intermediate register has a size of 16, 16 bits may be moved to one of two output registers (e.g. to a first output register).

As seen at block 890, once the first output register is full, its data may be transferred to storage. Alternatively, the output register data of a first and a second output register may be transferred together once both output registers are full. Other permutations may also be possible in accordance with the present invention. In one embodiment of the invention, the transfer of all output register data to storage (block 890) empties both output registers.

In the meantime, at block 855, samples may be collected from the second data stream. These samples may be collected into a second intermediate register.

At block 860, it is determined whether or not the second intermediate register is full. If the second intermediate register is not full, it may continue to receive samples from the data stream as described at block 855 above.

As seen at block 870, if the second intermediate register is determined to be full, its contents may be moved into an available output register. Continuing the above example, its contents may be moved into the second of two output registers while the first output register is full.

As seen at block 890, once the available output register is full, its data may be transferred to storage.

In the embodiment of the invention seen in FIGS. 7 and 8, components used to transfer data include a first intermediate register, at least one additional intermediate register, a first output register and at least one additional output register. One or any suitable combination of these components may be varied in accordance with the present invention. Moreover, although the Figures show the filling and emptying of the various registers in a particular order, the registers process data in any appropriate combination and in any appropriate order in accordance with the present invention.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to a method for increasing a pacing parameter of a mammalian heart. The present invention is also not limited to the transfer and storage of pacing data, per se, but may find further application as a data transfer and/or data storage means. The present invention further includes within its scope methods of making and using the data transfer and/or data storage means described hereinabove.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

We claim:

1. A method of transferring at least two data streams in a medical device, comprising:
   collecting first data stream data into a first intermediate register;
   collecting additional data stream data into at least one additional intermediate register;
   storing first intermediate register contents in a first output register;
   storing first intermediate register contents in at least one additional output register; and
   storing remaining first intermediate register contents in the first intermediate register if the additional output register is full.

2. The method of claim 1, further comprising:
   storing additional intermediate register contents in the first output register.

3. The method of claim 1 further comprising:
   storing additional intermediate register contents in at least one additional output register.

4. The method of claim 3 further comprising:
   storing remaining additional intermediate register contents in the additional intermediate register if the additional output register is full.

5. The method of claim 1 further comprising:
   storing first intermediate register contents with in identification code that uniquely identifies the first data stream data.

6. The method of claim 1 further comprising:
   storing additional intermediate register contents with an identification code that uniquely identifies the additional data stream data.

7. The method of claim 1 further comprising:
   transferring contents of the first output register to memory.

8. The method of claim 7 further comprising:
   transferring contents of an additional output register to memory.

9. The method of claim 1 further comprising:
   receiving compressed first data stream data.

10. The method of claim 1 further comprising:
    receiving compressed additional data stream data.

11. The method of claim 1 further comprising:
    collecting first data stream data until the first intermediate register is full.

12. The method of claim 1 further comprising:
    collecting additional data stream data until the additional intermediate register is full.

13. The method of claim 1 further comprising:
    storing remaining first intermediate register contents in the first intermediate register if the first output register is full.

14. The method of claim 1 further comprising:
    storing remaining additional intermediate register contents in the additional intermediate register if the first output register is full.

15. A method of transferring at least two data streams in a medical device, comprising:
    collecting first data stream data into a first intermediate register;
    collecting additional data stream data into at least one additional intermediate register;
    storing first intermediate register contents in a first output register; and
    storing first intermediate register contents in the first output register if the state of the first output register is empty, when the first intermediate register is full.

16. The method of claim 15 further comprising:
    storing first intermediate register contents in the additional output register if the state of the first output register is full.

17. The method of claim 15 wherein the additional intermediate register is full, further comprising:
    storing additional intermediate register contents in the first output register if the state of the first output register is empty.

18. The method of claim 17 further comprising:
    storing additional intermediate register contents in the additional output register if the state of the first output register is full.

19. A system for transferring at leant two data streams in a medical device, comprising:
    means for collecting first data stream data into a first intermediate register;
    means for collecting additional data stream data into at least one additional intermediate register;
    means for storing first intermediate register contents in a first output register;
    means for storing first intermediate register in at least one additional output register; and
    means for storing remaining first intermediate register contents in the first intermediate register if the additional output register is full.

20. The system of claim 19, further comprising:
    means for storing additional intermediate register contents in the first output register.

21. The system of claim 19, further comprising:
    means for storing first intermediate register contents with an identification code that uniquely identifies the first data stream data.

22. The system of claim 19, further comprising:
    means for storing additional intermediate register contents with an identification code that uniquely identifies the additional data stream data.

23. The system of claim 19, further comprising:
    means for transferring contents of the first output register to memory.

24. The system of claim 23, further comprising:
    means for transferring contents of an additional output register to memory.

25. The system of claim 19, further comprising:
    means for collecting first data stream data until the first intermediate register is full.

26. The system of claim 19, further comprising:
    means for collecting additional data stream date until the additional intermediate register is full.

27. The system of claim 19, further comprising:
    means for storing remaining first intermediate register contents in the first intermediate register if the first output register is full.

28. The system of claim 19, further comprising:

means for storing remaining additional intermediate register contents in the additional intermediate register if the first output register is full.

29. The system of claim 19, further comprising:

means for determining a state of the first output register.

30. A system for transferring at least two data streams in a medical device, comprising:

means for collecting first data stream data into first intermediate register;

means for collecting additional data stream data into at least one additional intermediate register;

means for storing first intermediate register contents in a first output register;

means for storing additional intermediate register contents in at least one additional output register; and means for storing remaining additional intermediate register contents in the additional intermediate register if the additional output register is full.

31. A computer usable medium including a program for transferring data in an implantable device, comprising:

computer program code that collects first data stream data into a first intermediate register;

computer program code that collects additional data stream data into at least one additional intermediate register;

computer program code that stores first intermediate register contents in a first output register;

computer program code that stores first intermediate register contents in at least one additional cutout register; and computer program code that stores remaining first intermediate register contents in the first intermediate register if the additional output register is full.

32. The program of claim 31, further comprising:

computer program code that stores additional intermediate register contents in the first output register.

33. The program of claim 31 further comprising:

computer program code that stores additional intermediate register contents in at least one additional output register.

34. The program of claim 33 further comprising:

computer program code that stores remaining additional intermediate register contents in the additional intermediate register it the additional output register is full.

35. The program of claim 31 further comprising:

computer program code that stores first intermediate register contents with an identification code that uniquely identifies the first data stream data.

36. The program of claim 31 further comprising:

computer program code that stores additional intermediate register contents with an identification code that uniquely identifies the additional data stream data.

37. The program of claim 31 further comprising:

computer program code that transfers contents of the first output register to memory.

38. The program of claim 37 further comprising:

computer program code that transfers contents of an additional output register to memory.

39. The program of claim 31 further comprising:

computer program code that receives compressed first data stream data.

40. The program of claim 31 further comprising:

computer program code that receives compressed additional data stream data.

41. The program of claim 31 further comprising:

computer program code that collects first data stream data until the first intermediate register is full.

42. The program of claim 31 further comprising:

computer program code that collects additional data stream data until the additional intermediate register is full.

43. The program of claim 31 further comprising:

computer program code that stores remaining first intermediate register contents in the first intermediate register if the first output register is full.

44. The program of claim 31 further comprising;

computer program code that stores remaining additional intermediate register contents in the additional intermediate register if the first output register is full.

45. The program of claim 31 further comprising:

computer program code that determines a state of the first output register.

46. The program of claim 45 wherein the first intermediate register is full, further comprising:

computer program code that stores first intermediate register contents in the first output register if the state of the first output register is empty.

47. The program of claim 46 further comprising:

computer program code that stores first intermediate register contents in the additional output register if the state of the first output register is full.

48. The program of claim 45 wherein the additional intermediate register is full, further comprising:

computer program code that stores additional intermediate register contents in the first output register if the state of the first output register is empty.

49. The program of claim 48 further comprising:

computer program code that stores additional intermediate register contents in the additional output register if the state of the first output register is full.

* * * * *

UNITED STATES PATENT AND TRADEMARK OFFICE
CERTIFICATE OF CORRECTION

| | |
|---|---|
| PATENT NO. | : 6,910,084 B2 |
| APPLICATION NO. | : 09/843915 |
| DATED | : June 21, 2005 |
| INVENTOR(S) | : Augustijn et al. |

It is certified that error appears in the above-identified patent and that said Letters Patent is hereby corrected as shown below:

Col. 23, line 10, delete "into first" and insert --into a first--

Signed and Sealed this

Third Day of April, 2007

JON W. DUDAS
*Director of the United States Patent and Trademark Office*